(12) United States Patent
Urano et al.

(10) Patent No.: US 7,399,816 B2
(45) Date of Patent: Jul. 15, 2008

(54) MALEIMIDYL-CONTAINING MATERIAL AND PRODUCTION METHOD THEREOF

(75) Inventors: Chisato Urano, Minamiashigara (JP); Yoshihiro Inaba, Minamiashigara (JP); Hiroshi Yamamoto, Minamiashigara (JP); Takako Kobayashi, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 435 days.

(21) Appl. No.: 11/129,851

(22) Filed: May 16, 2005

(65) Prior Publication Data

US 2006/0128943 A1    Jun. 15, 2006

(30) Foreign Application Priority Data

Dec. 15, 2004    (JP)    ............................ 2004-363266

(51) Int. Cl.
*C08F 26/02*    (2006.01)
(52) U.S. Cl. .................. 526/258; 526/317.1; 526/346; 525/375
(58) Field of Classification Search .............. 526/317.1, 526/258, 346; 525/375
See application file for complete search history.

(56) References Cited

U.S. PATENT DOCUMENTS 4,079,041 A * 3/1978 Baumann et al. ............ 526/258
4,544,621 A * 10/1985 Roth ........................ 430/271.1

FOREIGN PATENT DOCUMENTS

JP    11-106391    4/1999

OTHER PUBLICATIONS

J. Polym. Sci.: Polymer Chemistry Edition, vol. 17, 3675-3685 (1979).

* cited by examiner

*Primary Examiner*—Ling-Siu Choi
(74) *Attorney, Agent, or Firm*—Fildes & Outland, P.C.

(57) ABSTRACT

The invention provides a maleimidyl-containing material having a substituent group defined by the following structural formula (1) containing a maleimidyl group (maleimido group):

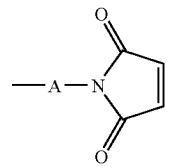

Formula (1)

wherein A denotes a spacer containing an amino acid or a peptide spacer P.

Also, the invention provides a production method of the above-mentioned maleimidyl-containing material involving a step of reacting a material containing an amino acid or a peptide chain with a compound containing a maleimido group.

20 Claims, No Drawings

MALEIMIDYL-CONTAINING MATERIAL AND PRODUCTION METHOD THEREOF

CROSS-REFERENCE TO RELATED APPLICATION

This application claims priority under 35 USC 119 from Japanese Patent Application No. 2004-363266, the disclosure of the incorporated by reference herein.

BACKGROUND OF THE INVENTION

1. Field of the Invention

The present invention relates to a maleimidyl-containing material and a production method thereof. More particularly, the invention relates to a maleimidyl-containing material usable for carriers of diagnosing drugs and pharmaceutical products; carriers for antigen/antibody fixation; chromatographic carriers; viscosity adjustment agents; resin molded materials; coating material additives; crosslinking/curing agents; and additives of cosmetics; and a production method thereof.

2. Description of the Related Art

Functional materials such as ion exchange resins and chelating resins have conventionally been used widely as carriers of various chemical substances. Such functional materials have a variety of reactive groups on the surface. Conventionally, various functional materials, into which active hydrogen-containing groups such as carboxyl, hydroxyl, and primary and secondary amino groups have been introduced, have been employed for various uses. In recent years, biomolecules such as nucleic acids, peptides, and antibodies or synthesized molecules analogous to biomolecules have been employed for affinity chromatography, diagnosing drugs, and inspection drugs while retaining activity and being fixed in materials. For such uses, carriers comprising maleimido groups capable of forming selective and stable bonds with SH groups of the biomolecules or the synthesized molecules analogous to biomolecules in moderate reaction conditions have been sought after. In the case of using materials with such a high selectivity as the carriers, it is required that they evenly and reliably bear a prescribed quantity of maleimido groups and also it is required that the materials have good dispersibility in a water-based medium in which the biomolecules are soluble.

As maleimido-containing compounds, maleimido-containing polystyrene particles are listed up in the 2001/2002 production brochure (p. 909) of Fulka Co. However, these materials have high hydrophobicity and therefore have very inferior dispersibility in a water-based medium.

In such a situation, Japanese Patent Application Laid-Open No. 11-106391 discloses fine particles bearing maleimido-containing phospholipid films on the surface so as not to lower the physiological activity of the biomolecules. The materials are produced as follows: producing in advance a maleimido-containing phospholipid by causing reaction of a bivalent reagent such as N-(6-maleimidocaproyloxy)succinimide having a succinimido group and a maleimido group in one molecule with a phospholipid, and refining the reaction product by column chromatography or the like; producing a maleimido-containing phospholipid film by subjecting the refined product to multi-step treatment; and forming the film on nucleating particles such as magnetic particles. However, the materials have physical disadvantages such as low solvent resistance since the nucleating particles and the maleimido-containing phospholipid films are not chemically bonded. Further, the manufacturing process is extremely complicated and the bivalent reagent, a raw material, is a costly reagent, thus increasing the cost.

As another production method, there is a method for producing the maleimidyl-containing material by reaction of a compound containing two maleimidyl groups in one molecule, such as 4,4'-bismaleimidodiphenylmethane, 1,2-bismaleimidoethane, and 1,6-bismaleimidohexane, with a material containing an SH group.

According to this method, since another maleimido group is further introduced at the time of introduction of one maleimido group, the obtained product becomes a material inferior in dispersibility in a water-based medium. Further, there are disadvantages in that the compound containing two maleimidyl groups in one molecule being a costly reagent results in increased costs and that the material containing the SH group, which is chemically instable, has to be produced in advance.

Further, a maleimidyl-containing material is produced by reaction of polystyrene and N-chloromethylmaleimide by a method described in J. Polym. Sci.: Polymer Chemistry Edition, vol. 17,3675-3685 (1979). According to the method, a maleimido group can be introduced by one-step reaction; however, since the mother material is polystyrene, the hydrophobicity is increased. Also, the method is not desirable in view of the use of harmful phosphorus trichloride to synthesize N-chloromethylmaleimide.

Accordingly, the maleimidyl-containing materials made available so far have been insufficient in the dispersibility in a water-based medium and no production method of a maleimidyl-containing material at a low raw material cost by simple process has been made developed till now.

SUMMARY OF THE INVENTION

The first aspect of the present invention is to provide a maleimidyl-containing material having a substituent group defined by the following structural formula (1) containing a maleimidyl group (maleimido group):

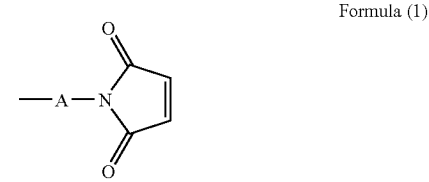

Formula (1)

wherein A denotes a spacer containing an amino acid or peptide spacer P.

The second aspect of the invention is to provide a production method of a maleimidyl-containing material as described in the first aspect, involving reacting an amino acid- or peptide chain-containing material with a compound containing a maleimidyl group.

DETAILED DESCRIPTION OF THE INVENTION

The present invention is for solving the above-mentioned conventional problems and provides a maleimidyl-containing material excellent in dispersibility in a water-based medium and a production method thereof.

The above-mentioned purpose can be accomplished by the invention. That is, a maleimidyl-containing material of the invention is characterized in that the material has a substituent group defined by the following structural formula (1) containing a maleimidyl group, particularly on the surface, or on the surface and inside of the material.

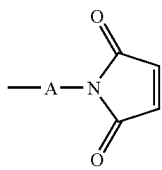

Formula (1)

wherein (A) denotes a spacer containing an aminoacid or peptide spacer P.

The maleimidyl-containing material of the invention is preferably embodied in one of the following embodiments.

In the first embodiment of the invention the spacer defined by (A) in the structural formula (1) comprises a spacer P and a spacer X of which the spacer X exists nearer to the maleimidyl group side than the spacer P and the spacer X is an aliphatic, aromatic, alicyclic, alicyclic-aliphatic, or aromatic-aliphatic spacer.

In the second embodiment of the invention the above-mentioned spacer X contains an ether bond.

In the third embodiment of the invention the above-mentioned spacer X contains an ester bond.

In the fourth embodiment of the invention the above-mentioned spacer X contains an amido bond.

In the fifth embodiment of the invention the above-mentioned spacer X contains one or more methylene groups [—$(CH_2)_n$— (n is a natural number of 1 or higher)].

In the sixth embodiment of the invention the above-mentioned maleimidyl-containing material consists of polymer particles.

In the seventh embodiment of the invention the abovementioned polymer particles are selected from a group consisting of (meth)acrylate polymers, styrene polymers, (meth)acrylate-styrene copolymers, and (meth)acrylate-acrylamide copolymers.

In the eighth embodiment of the invention the above-mentioned polymer particles have an average particle diameter of 0.01 μm to 500 μm.

In the ninth embodiment of the invention the above-mentioned maleimidyl-containing material consists of cross-linked polymer particles.

In the tenth embodiment of the invention the above-mentioned cross-linked polymer particles are selected from a group consisting of (meth)acrylate polymers, styrene polymers, (meth)acrylate-styrene copolymers, and (meth)acrylate-acrylamide copolymers.

In the eleventh embodiment of the invention the abovementioned cross-linked polymer particles have an average particle diameter of 0.01 μm to 500 μm.

In the twelfth embodiment of the invention the above-mentioned spacer P is an amino acid containing α-amino acid or a peptide containing α-amino acid.

In the thirteenth embodiment of the invention the above-mentioned spacer P is a peptide containing at least one of serine and tyrosine or an amino acid containing at least one of serine and tyrosine.

The production method of a maleimidyl-containing material of the invention is as follows.

The first production method of a maleimidyl-containing material is a maleimidyl-containing material production method involving reacting a material containing an amino acid or a peptide chain with a compound containing a maleimido group.

The second production method of a maleimidyl-containing material of the invention is a maleimidyl-containing material production method involving reacting a material containing an amino acid or a peptide chain with a hydroxyalkylmaleimide.

The third production method of a maleimidyl-containing material of the invention is a maleimidyl-containing material production method involving reacting a material containing an amino acid or a peptide chain with a hydroxymethylmaleimide.

The fourth production method of a maleimidyl-containing material of the invention is a maleimidyl-containing material production method involving reacting a material containing an amino acid or a peptide chain with a carboxyalkylmaleimide.

The fifth production method of a maleimidyl-containing material of the invention is a maleimidyl-containing material production method involving reacting a material containing an amino acid or a peptide chain with a maleic anhydride.

According to the invention, a maleimidyl-containing material with superior dispersibility in a water-based medium and a production method of a maleimidyl-containing material are provided.

The invention provides a maleimidyl-containing material having a substituent group defined by the following structural formula (1) containing a maleimidyl group (also called a "maleimido group"), particularly on the surface or on the surface and inside of the material:

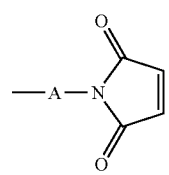

Formula (1)

wherein (A) denotes a spacer containing an amino acid or peptide spacer P.

By having the substituent group defined by the above-mentioned structural formula (1), the dispersibility in a water-based medium (e.g. pure water and a buffer solution) can be favorable. Particularly, if the material is produced using a biomolecule-philic mother material, a material having excellent dispersibility in biomolecules and biomolecule-soluble water-based media can be provided. The material can be used preferably for uses such as carriers of diagnosing drugs and pharmaceutical products; carriers for antigen/antibody fixation; chromatographic carriers; viscosity adjustment agents; resin molded materials; coating material additives; crosslinking/curing agents; and additives of cosmetics.

The length (the number of atoms) of (A) described above is preferably 1 to 12,5000. Also, the molecular weight of (A) is preferably 75 to 1,500,000.

The spacer defined by (A) in the structural formula (1) comprises a spacer P and a spacer X and the spacer X is preferably nearer to the maleimidyl group side than the spacer P. That is, the substituent group defined by the structural formula (1) is preferably a substituent group defined by the following structural formula (2). The maleimidyl-containing material can be produced by a simple method by inserting the spacer X between the spacer P and the maleimidyl group.

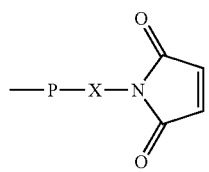

Formula (2)

The spacer X preferably contains an aliphatic, aromatic, alicyclic, alicyclic-aliphatic, or aromatic-aliphatic spacer.

The spacer X is preferable to contain an ether bond, an ester bond, an amido bond, and/or one or more methylene groups $[-(CH_2)_n-$ (n is a natural number of 1 or higher)]. The material can be produced at a low cost by introduction of these bond and/or groups.

The shape of the maleimidyl-containing material of the invention may be spherical, plate-shaped, needle-like, spindle-like, or amorphous. Also, while the size is not particularly limited, if the surface area is larger, the average particle diameter is preferably 0.01 µm to 500 µm, and more preferably 10 µm to 200 µm in consideration of the practical usability in the case of a spherical, plate-, or amorphous shape. In the case of needle-like or spindle-like shape, the material preferably has a longer axial length of 0.01 µm to 500 µm and an axial ratio of 3 to 20. Among these shapes, the spherical shape is preferable because of the easiness of production. Further, although the material does not have to have a cross-linked structure, it preferably to has a cross-linked structure so as to increase its solvent resistance. In consideration of production easiness and controllability of particle size distribution, the maleimidyl-containing material of the invention preferably has a substituent group defined by the structural formula (1) in the polymer particles or the cross-linked polymer particles. The preferable average particle diameter or the like is as described above. The average particle diameter can be measured by using a photograph taken by an optical microscope or an electron microscope.

As described above, the maleimidyl group is introduced through the spacer comprising an amino acid or peptide spacer P. As the amino acid or peptide chain-containing material (the material which does not yet have a maleimidyl substituent group), those having the amino acid or peptide chain (the spacer P) on the surface or on the surface and inside are preferable and examples are cross-linked (meth)acrylate polymers, styrene polymers, cross-linked polystyrene, cross-linked acrylamide polymers, cross-linked (meth)acrylate-styrene-acrylamide copolymers, core-shell type organic polymers, silica gel, cross-linked silicone resins, cross-linked agarose, cross-linked cellulose, and cross-linked dextran having amino acid or peptide chains, proteins such as KLH, BSA, and OVA, and their modified proteins. In this specification, (meth)acrylate means methacrylate and acrylate.

Among these, cross-linked (meth)acrylate polymers, styrene polymers, cross-linked acrylamide polymers, and cross-linked (meth)acrylate-styrene copolymers are more preferable since the material composition can be controlled easily.

In the case of polymer particles and cross-linked polymer particles, at least one selected from a group consisting of (meth)acrylate polymers, styrene polymers, (meth)acrylate-styrene copolymers, and (meth)acrylate-acrylamide copolymers is preferable.

The amino acid or peptide chain-containing polymer, which is one of the amino acid or peptide chain-containing materials, may be obtained by producing a polymer containing a hydroxyl, carboxyl, or amino group represented with Wang Resin and then bonding the amino acid or peptide chain thereto.

In the invention, the amino acid or peptide chain may contain a hydroxyl group such as serine and tyrosine. Further, bonding to the polymer, which will be described later, may be carried out on either the amino-terminal side or the carboxyl terminal side.

Typical examples to be used as the amino acid or as the amino acid composing the peptide chain are natural α-amino acids and practical examples are non-aromatic monoamino-monocarboxylic acids (neutral amino acids) such as glycine (three-letter abbreviation Gly, a single letter abbreviation G, same for the following), alanine (Ala, A), valine (Val, V), leucine (Leu, L), isoleucine (Ile, I), serine (Ser, S), threonine (Thr, T), cysteine (Cys, C), methionine (Met, M), proline (Pro, P), and cystine; non-aromatic monoaminodicarboxylic acids (acidic amino acids) such as glutamic acid (Glu, E), aspartic acid (Asp, D), glutamine (Gln, Q), and asparagine (Asn, N); non-aromatic diaminomonocarboxylic acids (basic amino acids) such as lysine (Lys, K) and arginine (Arg, R); aromatic neutral aminoacids such as phenylalanine (Phe, F), tryptophane (Trp., W), tyrosine (Tyr, Y); and aromatic basic amino acids such as histidine (His, H).

As derivatives of the above-exemplified natural α-amino acids, α-amino acid derivatives such as hydroxyproline, β,β-dimethylcysteine, phenylglycine, methylhistidine, acetyllysine, methionine S-oxide, methionine S,S-dioxide, pyroglutamine, and γ-carboxyglutamine are usable. These exemplified α-amino acids and their derivatives are preferably L-type optical isomers since such have biological activity. In addition to these, β-amino acids such as β-alanine; γ-amino acids such as γ-aminobutyric acid (abbreviation GABA) and carnitine; δ-amino acids such as δ-aminolevulinic acid and δ-amino-n-valeric acid; and amino sugar carboxylic acids such as muranic acid may be used. Further, retro-pseudo peptide structure may be formed by adding dicarboxylic acid such as malonic acid, succinic acid, and malic acid to peptide bond chains. Among these exemplified amino acids, 20 types of α-amino acids existing in nature are preferably used.

The spacer P in the structural formula (1) may comprise a plurality of types of peptide chains. The content of the peptide (the content of the amino acid or peptide chain-containing material) is generally 0.001 to 99%, and preferably 0.01 to 90% in terms of controllability of substrate-specific-philicity of the material, of the total organic components. The percentage by weight of the content can be measured by mass spectrometry of semiconductor super fine particles, thermogravitational analysis, or a combination of spectroscopy such as nuclear magnetic resonance spectoscopy (NMR) and infrared ray absorption spectroscopy (IR).

The spacer P is preferably peptides containing at least either serine or tyrosine or amino acids containing at least either serine or tyrosine since the maleimidyl-containing material can be produced easily by etherification reaction.

As the method of introducing the amino acid or peptide chain to the polymer, the following methods can be exemplified.

[Introduction of Peptide Chain by Amidation]

At first, there is a method of amidation to amino group or carboxyl bonded to a mother material (a material before the spacer P is introduced). This is a method of adopting amidation (hereinafter, referred to as amidation method) using a terminal group such as amino group or carboxyl group, as a reaction starting point.

Further, the amidation method can be classified into two types. One is a method of forming amido bonds between carboxyl terminal groups or amino terminal groups of previously prepared peptides and amino groups or carboxyl groups bonded to the mother material (hereinafter, referred to as OP amidation method) and the other is a method of consecutively forming amido bonds, using amino groups or carboxyl groups of bonded organic residual groups bonded to the mother material as starting points, with carboxyl groups or amino groups of aminoacids (hereinafter, referred to as consecutive amidation method). A partial structure of the desired peptide residual group (a partial peptide residual group or a single amino acid residual group) may be included in the material in advance.

To introduce a desired peptide chain to the material according to the invention, the above-mentioned two types of amidation methods may be combined in an optional number of steps and in an optional order. That is, for example, there are methods of (i) first bonding a partial structure of a desired peptide chain by the OP amidation method and then bonding the remaining portion structure to the terminal of the formed partial structure by the OP amidation method (a method of dividing the desired peptide chain into respective partial structures is not particularly limited and the desired peptide chain may be divided at optional peptide bonding sites into an optional number of the partial structures); (ii) first bonding a partial structure of a desired peptide chain by the OP amidation method and then repeating the consecutive amidation method so as to compose the remaining partial structure from the terminal of the formed partial structure (a method of dividing the desired peptide chain into respective partial structures is not particularly limited and the desired peptide chain may be divided at optional peptide bonding sites); and (iii) first forming a partial structure of a desired peptide chain by the consecutive amidation method and then bonding the remaining portion structure to the terminal of the formed partial structure by the OP amidation method (a method of dividing the desired peptide chain into respective partial structures is not particularly limited and the desired peptide chain may be divided at optional peptide bonding sites). Of course, the entire peptide synthetic reaction is first planned by dividing the desired peptide chain further into a large number of partial structures based on the necessity and the above-mentioned two types of amidation methods may be added in an optional number of steps in an optional order to the above exemplified three types of methods (i) to (iii).

The amidation reaction can be carried out by condensation of carboxyl or its derivative group (an ester, an acid anhydride, and an acid halide such as acid chloride) with an amino group. In the case an acid anhydride or an acid halide is used, a base is added so as to coexist. In the case an ester such as methyl ester or ethyl ester of a carboxylic acid is used, heating or pressure decrease is sometimes effective to remove produced alcohol. In the case carboxyl is directly amidated, an optional substance promoting the amidation reaction such as an amidation reagent, a condensation additive, or an active esterification agent may be added or preliminarily reacted beforehand.

Representative examples of the amidation reagent are carbodiimides such as N,N'-dicyclohexylcarbodiimide (so-called DCC), N,N'-diisopropylcarbodiimide (so-called DIC), 1-cyclohexyl-3-(2-morpholinoethyl)carbodiimide metho-p-toluenesulfonate (so-called Morpho-CDI), 1-(3-dimethylaminopropyl)-3-ethylcarbodiimide methiodide, and 1-ethyl-3-(3-dimethylaminopropyl)carbodiimide hydrochloride (so-called Water-soluble carbodiimide). Among these, 1-ethyl-3-(3-dimethylaminopropyl)carbodiimide hydrochloride is preferably used in a water-containing system or an alcohol type reaction system.

Examples of the condensation additive are 3,4-dihydro-3-hydroxy-4-oxo-1,2,3-benztriazoine, 1-hydroxybenztriazole (so-called HOBT), and N-hydroxy-5-norbornene-2,3-dicarboxyimide. Examples of the active esterification agent are compounds giving imidyl esters such as N,N'-bissuccinimidyl carbonate, N,N'-bissuccinimidyl oxalate, N-hydroxyphthalimide, and N-hydroxysuccinimide; compounds giving phenyl esters bonded with an electron attractive group such as p-nitrophenyl trifluoroacetate; and halophenols such as pentachlorophenol, pentafluorophenol, and 2,4,5-trichlorophenol.

[Use of Protection Group in Amidation Reaction]

In the above-mentioned two types of amidation methods, to selectively carry out the amidation reaction with the mother material, it is generally preferable to protect the amino group or carboxyl group of an oligopeptide or amino acid to be bonded by the amidation with a proper protection group. Such protection group is not particularly limited as long as it can be removed selectively thereafter (de-protection).

Practical examples of the protection group for the amino group are acyl groups for protection by forming aliphatic amido bond such as formyl, acetyl, chloroacetyl, dichloroacetyl, grichloroacetyl, trifluoroacetyl, acetoacetyl, and o-nitrophenylacetyl; aromatic acyl groups such as benzoyl and o-nitorbenzoyl; alkyl groups such as methyl, benzyl, and allyl; alkoxycarbonyl groups such as methoxycarbonyl, diisopropylmethyloxycarbonyl, isobutyloxycarbonyl, tert-butyloxycarbonyl (hereinafter abbreviated as BOC), and benzyloxycarbonyl (hereinafter abbreviated as CBZ); 2-haloethyloxycarbonyl groups such as 2,2,2-trichloroethyloxycarbonyl, 2-iodoethyloxycarbonyl and 1,1-dimethyl-2-chloroethyloxycarbonyl; ethyloxycarbonyl group bonded with electron attractive groups such as 1,1-dimethyl-2-cyanoethyloxycarbonyl and 1,1-dimethyl-2-nitroethyloxycarbonyl; CBZ group derivatives with improved stability of the BOC groups in the de-protection condition by improving acid resistance such as 2,4-dichlorobenzyloxycarbonyl, p-nitrobenzyloxycarbonyl, and p-cyanobenzyloxycarbonyl; alkoxycarbonyl groups having unsaturated bonds such as vinyloxycarbonyl and allyloxycarbonyl; and protection groups for protection by forming carbamate bonds such as aryloxycarbonyl, e.g. phenoxycarbonyl and m-nitrophenoxycarbonyl; groups for protection by forming phthalimido group; and 9-fluorenylmethyloxycarbonyl (hereinafter abbreviated as Fmoc group). Among them, BOC group and Fmoc group are preferably used.

Practical protection state of the carboxyl group may generally include alkyl ester bonds such as methyl ester, ethyl ester, tert-butyl ester, 2,2,2-trichloroethyl ester, and benzyl ester; aryl ester bonds such as phenyl ester and p-nitrophenyl ester; and silyl ester bonds such as trimethylsilyl ester and tert-butyldimethylsilylester and among these, alkyl ester bonds such as methyl ester, ethyl ester, tert-butyl ester, and benzyl ester and aryl ester bonds such as p-nitrophenyl ester are preferably used and above all, methyl ester and ethyl ester are more preferably used.

[Consecutive Amidation Method Using Protection Group]

The above-mentioned consecutive amidation method can be carried out more efficiently by a method using the above-mentioned protection groups. That is, the method is carried out by repeating the following steps in the following order: amidation of condensing an amino acid whose amino group or carboxyl group is protected by a protection group; a first refining step of separating the material subjected to the amidation; de-protection by removing the protection group; and a second refining step of separating the material subjected to de-protection.

That is, one amino acid residue is amido-bonded and the amino group or carboxyl group contained in the obtained amino acid residue structure become a reaction point of the next amidation. Preferably, the amino acid of which the amino group is protected by the protection group is used for the amidation. This is because in the case only natural α-amino acid is used as a raw material, the peptide residual group to be formed will have an amino terminal, and thus it is preferable in terms of bioactivity in some cases.

The peptide-containing mother material obtained in the above-mentioned manner (the amino acid- or peptide chain-containing material) is reacted with a maleimide compound, so that the maleimido group can be bonded to the spacer P (in the case the spacer X exists, bonded to the spacer X) and thus the maleimidyl-containing material (maleimido-containing polymer particles) of the invention can be obtained. The reaction can be carried out by causing reaction of a hydroxyl, carboxyl, or amino group in the peptide with the maleimide compound. Practically, it is produced by a process of causing reaction of the amino acid- or peptide chain-containing material with one of hydroxyalkylmaleimide, hydroxymethylmaleimide, carboxylalkylmaleimide, and maleic anhydride.

The reaction temperature at the time of reaction with hydroxyalkylmaleimide is preferably 25 to 180° C.: the reaction temperature at the time of reaction with carboxylmaleimide is preferably 0 to 180° C.: and reaction temperature at the time of reaction with maleic anhydride is preferably 0 to 100° C. The reaction is preferably carried out in an inert gas. The amount of the maleimidyl group in the maleimidyl-containing material is preferably 0.001 to 5 mmol/g in the entire amount.

The reaction of the hydroxyl in the peptide may be etherification with hydroxyl-containing maleimide compounds or esterification with carboxyl-containing maleimide. The reaction to the carboxyl in the peptide may be esterification with hydroxyl-containing maleimide compounds. The reaction to amino group in the peptide may be amidation with carboxyl-containing maleimide compounds or reaction with maleic anhydride.

Examples of the above-mentioned hydroxyl-containing maleimide compounds include hydroxyalkylmaleimides. Alkyl groups in the hydroxyalkylmaleimides are preferably alkyl groups having 1 to 20 carbon atoms and more preferably alkyl groups having 1, 2, or 3 carbon atoms in terms of excellent water-dispersibility. That is, as the hydroxyalkylmaleimides, hydroxymethylmaleimide, hydroxyethylmaleimide, and hydroxypropylmaleimide are preferable.

Examples of the carboxyl-containing maleimides are N-maleylamino acids obtained by reaction of amino acids and maleic anhydride and successive dehydration condensation. Among them, N-carboxymethylmaleimide, N-carboxyethylmaleimide, and N-carboxypropylmaleimide are preferable because the raw materials are economical.

The above-mentioned etherification, esterification, and amidation are carried out in the presence of a catalyst. Acidic or basic well-known catalysts can be used for the reaction. Examples usable as the basic catalysts are hydroxides, oxide, carbonates, and dicarbonates of alkali metals and alkaline earth metals and they may be used alone or two or more of them may be used in form of a mixture. Examples usable as the acidic catalysts are inorganic acids such as sulfuric acid, hydrochloric acid, nitric acid, and phosphoric acid; and organic acids such as p-toluenesulfonic acid, trichloroacetic acid, and acetic acid. Solid acid such as hydrotalcite-group minerals may also be used.

In the case of using a basic catalyst or an acidic catalyst, the use amount of the catalyst to the maleimide is 0.01 to 40% by weight, and preferably 0.1 to 15% by weight on the basis of the base or acid.

In the case of a solid catalyst, the use amount is 0.001 to 100% by weight, and preferably 0.1 to 50% by weight to the maleimide. The catalysts may be used in a state in which they are dissolved evenly or in a state in which they are not dissolved and in the case of the evenly dissolved state, their use amounts can be reduced. On the other hand, in the un-solved state, the catalysts can easily be separated and recovered from a reaction solution by a common method after reaction.

EXAMPLES

The present invention will be explained detail with reference to the following examples. However, it is not intended that the invention be limited to the illustrated examples. Modifications and substitutions to specific process conditions and structures can be made without departing from the spirit and scope of the invention. The "parts" in the examples means "parts by mass".

Synthesis Example 1

Synthesis of Hydroxymethylmaleimide

When maleimide (manufactured by Aldrich Chemical Co., Inc.) of 24 parts, 35% HCOH (manufactured by Wako Pure Chemical Industries, Ltd.) of 21 parts, and an aqueous 5% NaOH solution of 0.7 parts are mixed and reacted at 40° C. for 2 hours to precipitate hydroxymethylmaleimide in the form of a white crystal. The produced hydroxymethylmaleimide is filtered in reduced pressure and vacuum dried at room temperature. The crude crystal of hydroxymethylmaleimide obtained in such a manner is recrystallized in ethyl acetate to obtain hydroxymethylmaleimide of 22 parts.

Synthesis Example 2

Synthesis of Carboxymethylmaleimide

A solution obtained by dissolving maleic anhydride (manufactured by Wako Pure Chemical Industries, Ltd.) of 42 parts in acetic acid of 175 parts is added to a dispersion containing glycine of 32 parts and acetic acid of 510 parts. After 3 hours reaction at room temperature, maleamic acid precipitated in the form of a white solid is separated by filtration. The solid is washed with cold water and dried to obtain a solid of 71 parts. The obtained maleamic acid of 3 parts is dispersed in triethylamine of 3.6 parts and toluene of 500 parts and dehydrated for 1 hour under refluxing condition. After spontaneous cooling, the toluene is separated by decantation and an orange-color oil phase is dried under reduced pressure. After the obtained product is dissolved in a hydrochloric acid solution and the pH of the solution is adjusted to 2 or lower, ethyl acetate extraction is carried out. The extract is dried by dehydrated magnesium sulfate and the solvent is removed by vacuum distillation to obtain carboxymethylmaleimide of 1.2 parts.

Synthesis Example 3

Synthesis of Peptide-containing Material—OP Amidation Method

Wang resin (1% DVB, 38 to 75 μm, manufactured by Wako Pure Chemical Industries, Ltd.) of 3 parts is dispersed in N,N'-dimethylacetamide (DMA) of 30 parts. Further, N,N'-diisopropylcarbodiimide of 6 parts and glutathione (manufactured by Wako Pure Chemical Industries, Ltd.) of 9 parts are added and reaction is carried out at 40° C. for 18 hours. The particles obtained after the reaction are separated by filtration and repeatedly washed with DMA and methanol. The obtained particles are dried at 60° C. for 6 hours by a vacuum drier to obtain glutathione particles of 2 parts.

Synthesis Example 4

Synthesis of Peptide-containing Material—Consecutive Amidation Method 1

(Fmoc Amino Acid Condensation Reaction)

Fmoc leucine (manufactured by Wako Pure Chemical Industries, Ltd.) of 4.5 parts and 1-hydroxybenztriazole of 1.5 parts are dispersed in N,N'-dimethylformamide (DMF) of 25 parts. Further, the dispersion is put on an ice bath and N,N'-diisopropylcarbodiimide of 1.6 parts is added and the mixture is stirred for 30 minutes. Further, Wang resin (1% DVB, 38 to 75 μm, manufactured by Wako Pure Chemical Industries, Ltd.) of 5 parts is added and reaction is carried out at 25° C. for 18 hours. The particles obtained after the reaction are separated by filtration and repeatedly washed with methylene chloride and 2-propanol.

(De-Fmoc Reaction)

The obtained particles are dissolved in 50% piperidine/DMF of 50 parts and subjected to filtration two times to release the Fmoc group. After that, the particles are separated by filtration ad repeatedly washed with methylene chloride and 2-propanol.

Fmoc-glycine, Fmoc-phenylalanine, and Fmoc-tyrosine (tBu) are repeatedly subjected to Fmoc-amino acid condensation reaction and de-Fmoc reaction. After removal of the tBu group of the tyrosine by a TFA solution, the obtained particles are vacuum-dried at 60° C. for 6 hours to obtain peptide particles of 3.5 parts.

Synthesis Example 5

Synthesis of Peptide-containing Material—Consecutive Amidation Method 2

Similarly to the synthesis example 4, Fmoc-amino acid is condensed successively with Fmoc-leucine, Fmoc-glycine, Fmoc-phenylalanine, and Fmoc-lysine (BOC). The BOC group of the lysine is released from the obtained particles by a TFA solution to obtain peptide particles.

[Quantitative Analysis of Maleimidyl Group in the Material]

The maleimido group in the material is quantitatively measured by the following operation and calculation.

[Operation]
(1) Preparation of reaction reagent: a 100 ml volumetric flask is loaded with 0.5 ml/L 2-mercaptoethylamine solution of 20 ml and an aqueous solution of 0.1 mol/L sodium dihydrogen phosphate of 5 ml and filled with an aqueous solution of 50 mmol/L EDTA-2Na.
(2) A sample of 0.05 g is weighed and put in a 30 ml sample tube.
(3) The reaction reagent of 20 ml is added to the sample tube and the mixture is stirred at 25° C. for 1 hour with a stirrer.
(4) After the reaction, the sample tube is centrifuged to centrifugally precipitate particles.
(5) The supernatant solution of 0.08 ml is pored to a 50 ml volumetric flask. Further, the aqueous solution of 0.1 mol/L sodium dihydrogen phosphate of 2 ml and a 5 mmol/L 4-PDS-EtOH solution of 1 ml are added and the volumetric flask is filled with water to the top measurement line.
(7) The solution is transferred to the 50 ml sample tube from the 50 ml volumetric flask and stirred at 25° C. for 20 min.
(8) The solution is subjected to an absorptiometer to measure peak intensity at 324 nm. The measured value is set to be value 1.
(9) In the value 1 measurement, the same operation is carried out without adding any sample and the obtained value is set to be value 0.

[Calculation]
(1) The value A is calculated by subtracting the value 1 from the value 0.
(2) The value B is calculated from the value A according to an equation.

$$B=(A-0.0198)/25800$$

(3) The value C is calculated from the value B according to an equation.

$$C=B\times(50\times15/(0.08\times1000))\times1000$$

(4) The value calculated by dividing C by the sample amount (g) is determined to be the maleimido group amount (mmol/g) in the material.

Example 1

(Maleimidyl-containing Material Having Ether Bond)

The OH-containing peptide particles obtained in the synthesis example 4 of 10 parts is mixed with hydroxymethyl-maleimide synthesized in the synthesis example 1 of 17 parts and toluene of 500 parts and heated and stirred at 60 to 70° C. and further mixed with hydrated p-toluenesulfonic acid of 0.4 parts, as a catalyst, and the mixture is heated and refluxed for 8 hours to carry out reaction. The obtained fine particles are dispersed in and washed with methanol, further washed with ion-exchanged water and a solvent, and isolated and dried to obtain a maleimidyl-containing material. The amount of maleimidyl group of the maleimidyl-containing material obtained in such a manner is measured by the above-mentioned method.

The amount of maleimidyl group of the material is 0.3 mmol/g. The particles of 1 part are put in pure water of 10 parts and subjected to supersonic wave treatment for 30 seconds and observed by a microscope to confirm good dispersibility of the material.

Example 2

(Maleimidyl-containing Material Having Ester Bond)

The OH-containing peptide particles obtained in the synthesis example 4 of 10 parts is mixed with carboxymethyl-maleimide synthesized in the synthesis example 2 of 10 parts and toluene of 500 parts and further mixed with phosphoric acid of 0.5 parts, as a catalyst, and the mixture is refluxed for 10 hours to carry out reaction. The amount of maleimidyl group of the obtained material (a maleimidyl-containing material) is 0.2 mmol/g. The particles of 1 part are put in pure water of 10 parts and subjected to supersonic wave treatment for 30 seconds and observed by a microscope to confirm good dispersibility of the material.

Example 3

(Maleimidyl-containing Material Having Amido Bond)

The $NH_2$ group-containing peptide particles obtained in the synthesis example 5 of 10 parts is mixed with carboxymethylmaleimide synthesized in the synthesis example 2 of 10 parts and toluene of 500 parts and further mixed with phosphoric acid of 0.5 parts, as a catalyst, and the mixture is refluxed for 10 hours to carry out reaction. The amount of maleimidyl group of the obtained material (a maleimidyl-containing material) is 0.3 mmol/g. The particles of 1 part are put in pure water of 10 parts and subjected to supersonic wave treatment for 30 seconds and observed by a microscope to confirm good dispersibility of the material.

Example 4

(Maleimidyl-containing Material to be Produced by Reaction of Maleic Anhydride)

The $NH_2$ group-containing peptide particles obtained in the synthesis example 5 of 10 parts is mixed with acetic acid of 100 parts and further with maleic anhydride of 10 parts and reaction is carried out for 18 hours at a room temperature. The obtained fine particles are dispersed in and washed with methanol, further washed with ion-exchanged water and a solvent, and isolated and dried to obtain particles (an intermediate product).

The particles obtained in the above-mentioned reaction of 10 parts is dissolved in toluene of 500 parts and further mixed with triethylamine of 10 parts and the mixture is refluxed at 130° C. for 3 hours. The obtained fine particles are dispersed in and washed with methanol, further washed with ion-exchanged water and methanol, and isolated and dried to obtain particles (a maleimidyl-containing material).

Comparative Example (Maleimidyl-containing Material Having no Peptide Chain)

Wang resin (1% DVB, 38 to 75 μm, manufactured by Wako Pure Chemical Industries, Ltd.) of 10 parts is mixed with hydroxymethylmaleimide synthesized in the synthesis example 1 of 17 parts and toluene of 500 parts and heated and stirred at 60 to 70° C. and further mixed with hydrated p-toluenesulfonic acid of 0.4 parts, as a catalyst, and the mixture is heated and refluxed for 8 hours to carry out reaction. The obtained fine particles are dispersed in and washed with methanol, further washed with ion-exchanged water and a solvent, and isolated and dried to obtain a maleimidyl-containing material.

The amount of maleimidyl group of the maleimidyl-containing material obtained in such a manner is 0.1 mmol/g. The particles of 1 part are put in pure water of 10 parts and subjected to supersonic wave treatment for 30 seconds and observed by a microscope to confirm that the particle agglomerates are not parted from one another and the material is inferior in dispersibility.

As is clear from the above-mentioned results of the examples, the maleimidyl-containing material of the invention is excellent in water-dispersibility. Maleimidyl-containing polymer particles with good controllability in the maleimidyl group content and good dispersibility in a water-based medium can be obtained safely at a low cost.

What is claimed is:

1. A maleimidyl-containing material having a substituent group defined by the following structural formula (1) containing a maleimidyl group:

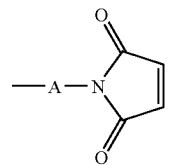

Formula (1)

wherein (A) denotes a spacer containing an amino acid or peptide spacer P.

2. The maleimidyl-containing material of claim 1 having a substituent group defined by the structural formula (1) containing a maleimidyl group on the surface, or on the surface and inside.

3. The maleimidyl-containing material of claim 1, wherein the spacer defined by (A) in the structural formula (1) comprises a spacer P and a spacer X and the spacer X exists nearer to the maleimidyl group side than the spacer P and the spacer X is an aliphatic, aromatic, alicyclic, alicyclic-aliphatic, or aromatic-aliphatic spacer.

4. The maleimidyl-containing material of claim 3, wherein the spacer X has an ether bond.

5. The maleimidyl-containing material of claim 3, wherein the spacer X has an ester bond.

6. The maleimidyl-containing material of claim 3, wherein the spacer X has an amido bond.

7. The maleimidyl-containing material of claim 3, wherein the spacer X has one or more methylene groups.

8. The maleimidyl-containing material of claim 1, wherein maleimidyl-containing material consists of polymer particles.

9. The maleimidyl-containing material of claim 8, wherein the polymer particles are selected from the group consisting of (meth)acrylate polymers, styrene polymers, (meth)acrylate-styrene copolymers, and (meth)acrylate-acrylamide copolymers.

10. The maleimidyl-containing material of claim 8, wherein the polymer particles have an average particle diameter of 0.01 μm to 500 μm.

11. The maleimidyl-containing material of claim 1, wherein the maleimidyl-containing material consists of cross-linked polymer particles.

12. The maleimidyl-containing material of claim 11, wherein the cross-linked polymer particles are selected from the group consisting of (meth)acrylate polymers, styrene polymers, (meth)acrylate-styrene copolymers, and (meth)acrylate-acrylamide copolymers.

13. The maleimidyl-containing material of claim 11, wherein the cross-linked polymer particles have an average particle diameter of 0.01 μm to 500 μm.

14. The maleimidyl-containing material of claim 1, wherein the spacer P is an amino acid containing α-amino acid or a peptide containing α-aminoacid.

15. The maleimidyl-containing material of claim 1, wherein the spacer P is a peptide containing at least one of serine and tyrosine or an amino acid containing at least one of serine and tyrosine.

16. A production method of the maleimidyl-containing material described in claim 1 comprising reacting a material containing an amino acid or a peptide chain with a compound containing a maleimidyl group.

17. The production method of a maleimidyl-containing material of claim 16, wherein the compound containing the maleimidyl group is a hydroxyalkylmaleimide.

18. The production method of a maleimidyl-containing material of claim 16, wherein the compound containing the maleimidyl group is hydroxymethylmaleimide.

19. The production method of a maleimidyl-containing material of claim 16, wherein the compound containing the maleimidyl group is a carboxylalkylmaleimide.

20. A production method of the maleimidyl-containing material described in claim 1 comprising reacting a material containing an amino acid or a peptide chain with a maleic anhydride.

* * * * *